(12) United States Patent
Carlsson et al.

(10) Patent No.: US 6,599,297 B1
(45) Date of Patent: Jul. 29, 2003

(54) DEVICE FOR VENTILATING THE MIDDLE EAR

(75) Inventors: Lennart Carlsson, Mölndal (SE); Matthew Yung, Ipswich (GB)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/485,992

(22) PCT Filed: Sep. 12, 1997

(86) PCT No.: PCT/SE97/01447
§ 371 (c)(1),
(2), (4) Date: Jul. 11, 2000

(87) PCT Pub. No.: WO99/13811
PCT Pub. Date: Mar. 25, 1999

(51) Int. Cl.[7] ............................................. A61F 11/00
(52) U.S. Cl. ..................... 606/109; 604/8; 604/174; 604/264; 606/108
(58) Field of Search ............... 604/264, 19, 22, 604/523, 93.01, 540, 8, 265, 285, 174, 175; 606/108, 109.2, 167, 185, 53, 60, 65, 72, 73, 76, 96; D24/173

(56) References Cited

U.S. PATENT DOCUMENTS

| | | | |
|---|---|---|---|
| 4,169,470 A | * 10/1979 | Ender et al. .................. | 128/92 |
| 4,640,271 A | * 2/1987 | Lower ........................... | 128/92 |
| 5,122,133 A | * 6/1992 | Evans ........................... | 606/73 |
| 5,192,293 A | * 3/1993 | Cartwright et al. .......... | 606/172 |
| 5,254,120 A | * 10/1993 | Cinberg et al. .............. | 606/109 |
| 5,372,583 A | * 12/1994 | Roberts et al. .............. | 604/51 |
| 5,496,329 A | * 3/1996 | Reisinger ..................... | 606/109 |
| 5,562,688 A | * 10/1996 | Riza ............................. | 606/148 |
| 5,573,008 A | * 11/1996 | Robinson et al. ............ | 128/754 |
| 5,716,358 A | * 2/1998 | Ochoa et al. ................. | 606/62 |

FOREIGN PATENT DOCUMENTS

WO   WO 93/10729   * 6/1993   ........... A61F/11/00

* cited by examiner

*Primary Examiner*—Brian L. Casler
*Assistant Examiner*—Jennifer Maynard
(74) *Attorney, Agent, or Firm*—Connolly Bove Lodge & Hutz LLP

(57) ABSTRACT

The invention relates to a device for ventilating the middle ear by means of a ventilation tube which is made of a tissue-compatible material, preferably titanium, and with a through-channel for air communication between the cavity of the middle ear and the outside air. The ventilation tube comprises, on the one hand, a front portion (2) which is arranged to be introduced into bone tissue and is designed so that a permanent anchoring is obtained in the bone tissue, and, on the other hand, a rear portion (6) which forms a passage through the skin. The ventilation tube further comprises an outer tube (1) which is made of the said tissue-compatible material and an inner tube (8) which is arranged releasably in the outer tube and whose inner bore forms the said through-channel (14) for air communication between the cavity of the middle ear and the outside air.

10 Claims, 1 Drawing Sheet

DEVICE FOR VENTILATING THE MIDDLE EAR

Figure 1:
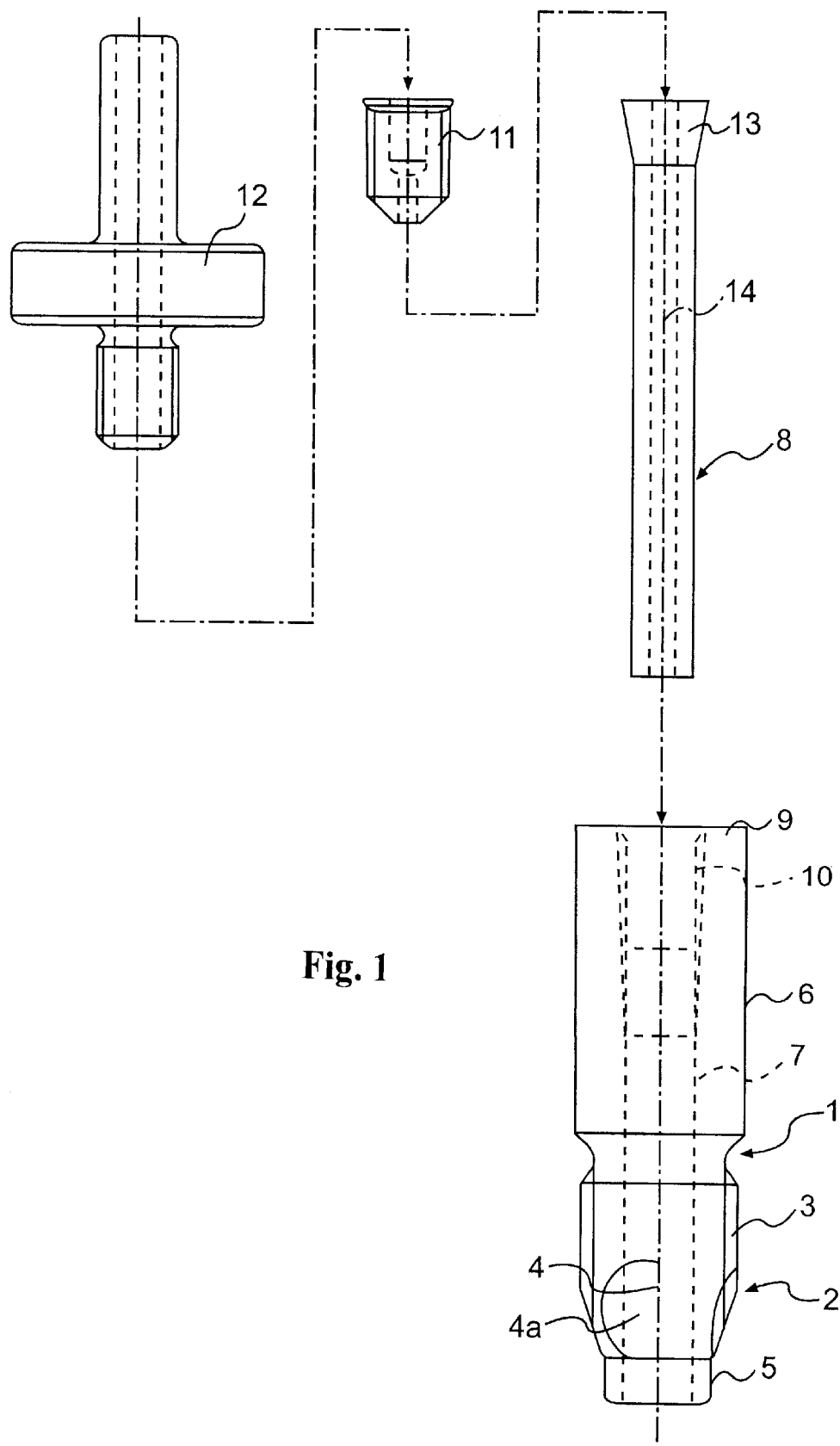

This application is a 371 of PCT/SE97/01447 field Sep. 12, 1997, and published as WO99/13811.

The present invention relates to a device for ventilating the middle ear by means of a ventilation tube which is made of a tissue-compatible material, preferably titanium, and which has a through-channel for air communication between the cavity of the middle ear and the outside air.

As is known, the function of the middle ear is to transmit sound energy from the environment to the inner ear, where the sound signals undergo complex processes of interpretation. This transmission of sound energy from the environment to the inner ear requires an impedance conversion of the sound signal, since the sound energy is being conveyed from one medium (air) to another medium (liquid) which is located in the inner ear and which has a considerably higher impedance than air. With the aid of the auditory ossicles and the shape of the surrounding organs, an impedance conversion takes place in the middle ear. A basic condition if normal hearing is to be maintained is that the normal impedance in the middle ear is retained and that the movement in the transmission chain is not damped, which necessitates a normally ventilated middle ear.

One of the commonest complaints seen in otology is, however, accumulation of liquid in the middle ear, which results in diminished hearing. This is especially common among children but also occurs in adults with chronic inflammation of the middle ear. Puncturing the tympanic membrane and fitting a ventilation tube is therefore a common operation. In the USA alone, approximately one million operations of this type are performed each year. In total, some 5 million ventilation tubes are used each year for these operations in Western Europe, the USA and Japan, most of these being performed on children under anaesthesia.

Some of these children with middle ear problems do not improve as they grow older, and instead the problems remain and become chronic in the adult years. The result is that the function of the middle ear is gradually destroyed. In most cases there is a progressive destruction of the middle ear, with consequently impaired hearing, gradually leading to severe hearing loss. These patients are normally helped initially by means of a tube through the tympanic membrane in a traditional manner, but the tube is expelled after a short time and the tympanic membrane becomes more and more damaged by these repeated treatments, and for this reason the method does not help the patient in the long run. It would therefore be desirable to devise a method by which it is possible to ensure ventilation of the tympanic membrane in these patients too.

A standard procedure here is the restoration of the middle ear, which involves removing excess connective tissue and enlarging the middle ear by excising bone, primarily in the mastoid area. This surgery increases the chances of the patient acquiring better hearing, but it has to be combined with an air channel for successful results. The surgical intervention is relatively extensive and cannot be repeated simply to make a diagnosis of the condition of the middle ear. It would therefore be desirable to have access to a channel which is large enough to accommodate a fibre optic instrument for examining the condition of the middle ear.

Where the normal method of ventilation via the tympanic membrane cannot be used, other methods have been tried, among others ventilation lines through the Eustachian tube or ventilation tubes at the margin of the tympanic membrane, i.e. between bone and soft tissue. However, none of these methods has been successful and come into general use.

With the aim of reducing the risk of expulsion and thus avoiding repeated surgical interventions, it is also already known to design the ventilation tube in the tympanic membrane with an outer surface made of titanium. The metal titanium has, as is known, been found to have unique properties of biocompatability with the body tissues. Different areas of clinical application have been tried out with success. Fixtures of various types which are anchored in the bone are used to secure various types of prostheses, for example dental prostheses in the jawbone of the oral cavity, and hearing aids anchored in the bone of the skull. In both cases, the titanium surface adapts extremely well both to the bone tissue and also, respectively, to the mucous membrane of the oral cavity or the skin.

The metal titanium, with its excellent biocompatibility properties, has also been shown to have relatively high affinity for binding blood products and forming tissue even on surfaces which are not primarily in contact with tissue. Among other things, this has led to ventilation tubes, placed in the tympanic membrane, becoming blocked more easily if they are made of titanium rather than of polymer material. In addition, a tube fitted in the tympanic membrane is in practice impossible to clean since the tympanic membrane is sensitive to contact.

Swedish Patent Application 8703694-3 describes a ventilation tube for temporary healing into the tympanic membrane, which consists of a plastic tube whose outer side has been provided with a continuous coating of titanium oxide. Alternatively, the ventilation tube can consist of a titanium tube whose inner air channel has been treated with a layer which annuls titanium's normal affinity for body secretions and body tissues, with the aim of preventing blockage of the ventilation channel.

Although the described ventilation tube has advantages over conventional ventilation tubes made of titanium, this type of ventilation tube does not represent a solution in those cases where a permanent anchoring is sought. In this case too, a certain amount of blockage of the ventilation channel takes place sooner or later, and this makes cleaning necessary.

Especially in the case of adults with chronic inflammation of the middle ear, there is at the present time no satisfactory method for obtaining the desired ventilation of the middle ear.

The aim of the present invention is to remedy the difficulties described hereinabove and to create a permanent ventilation channel for the middle ear.

According to the invention, this aim can be achieved by virtue of the fact that the ventilation tube is designed such that it can be anchored in the bone tissue, for example in the mastoid bone. The ventilation tube therefore comprises, on the one hand, a front portion which is arranged to be introduced into the bone tissue and is designed so that a permanent anchoring of the ventilation tube is obtained, and, on the other hand, a rear portion which forms a passage through the skin. In addition, the ventilation channel is preferably designed in such a way that blocking is minimized through both the design of the outer tube and the choice of material for the inner channel of the ventilation tube. The ventilation channel is also designed in such a way that it is possible to monitor the course of the disease in the middle ear using fibre optics and in this way to improve the result of treatment.

According to one advantageous embodiment, the ventilation tube comprises an outer tube which is made of tissue-compatible material with the ability to grow firmly into the bone tissue and to function in the external and the internal epithelial passage. The ventilation tube further comprises an inner tube which is introduced into the outer tube and which has the necessary properties for minimizing blockage. This inner tube is additionally releasable in order to permit cleaning or replacement without causing damage to the supporting tissue. When the inner tube has been removed, a channel is obtained through the ventilation tube which is large enough to allow the middle ear to be examined by fibre optics.

According to a further embodiment, the inner tube is provided with a membrane so that the ventilation of gas (for example air, water vapour) can be permitted while, by contrast, liquid and particles/bacteria are prevented from entering. In this case too, the inner tube (the insert) is easy to replace.

According to a third embodiment, the outer tube is designed such that its inner end is free in the excavated bone, for example the mastoid bone, and that it is surface-modified in order to make the ingrowth of tissue more difficult across the inner end of the tube. Such surface-coating can be obtained by known surface-coating methods, for example by sputtering, and with known materials, for example polyurethane or silicon.

In all the embodiments, the outside of the outer tube is designed in such a way that mechanical stability against the bone tissue is obtained during the healing phase, which is a precondition for osteointegration.

The invention is explained in greater detail hereinbelow, with reference to the attached drawing which shows an example of an expedient embodiment according to the invention.

The ventilation tube consists of an outer tube 1 which is made of titanium, and with the surface made of titanium oxide which is formed spontaneously on production. The outer tube comprises a front portion 2 with an external thread 3 arranged to be introduced into a hole made in the bone of the middle ear, so that the ventilation tube obtains a good mechanical stability against the surrounding bone tissue during a healing phase. This is a precondition for osteointegration and permanent anchoring of the ventilation tube. The threaded portion is designed at the very front with cutting edges 4 in order to permit a certain degree of self-tapping/scraping of bone material from the surrounding bone tissue when the tube is introduced into the pre-drilled hole in the bone, and cavities 4a for accommodating bone shavings which have been removed.

The insertion end 5 of the front portion is unthreaded and has a slightly rounded edge towards the inner bore 14 in order to prevent material from being scraped loose from the inner tube 8 and ending up in the middle ear when the inner tube is disengaged. After application, this unthreaded part extends a short distance into the middle ear and this free end is therefore surface-coated with, for example, a polymer material for preventing overgrowth of tissue, for example polyurethane or silicon.

The ventilation tube further comprises a rear portion 6 whose outer surface has a suitable shape for passing through the skin, and which portion is of such a length that after anchoring of the ventilation tube in the bone tissue, it is arranged to extend from the bone/skin interface, through the skin and out into the open air.

Extending though the ventilation tube there is a continuous bore or channel 7 in which an inner tube 8 made of polymer material, for example polyurethane or Teflon, is to be applied.

The opposite end 9 of the outer tube 1 is designed with an attachment thread 10 for attachment of an assembly instrument for screwing the ventilation tube into the bone. This attachment thread can additionally be used for other purposes, such as the attachment of various inserts, for example filters, membranes or capillaries 11 of types known per se. It can additionally be used for attachment of an air pump (indicated by the nipple 12 in the figure) for forced ventilation of the middle ear, should the need arise. Another area of application for the said attachment thread 10 is to form an attachment for a plug, the insert 11 being made solid. The bore 7 through the outer tube has such a diameter that a fibre optic instrument can be introduced for examining the middle ear.

The inner tube 8 has a length which is adapted to the length of the outer tube so that a certain free end is exposed in the middle ear when the inner tube has been pushed fully into the outer tube. The inner tube is further provided with a flange 13 whose greatest diameter exceeds the diameter of the bore 7, so that the inner tube is prevented from coming too far into the middle ear. The inner tube can be easily replaced or taken out for cleaning. Moreover, the diameter and length are chosen so that liquid cannot readily pass through the inner channel 14 when showering and washing. Instead of the said separate filters, membranes or capillaries 11, these can, for example a membrane, be incorporated in the inner tube. Such a membrane prevents water and bacteria from entering and seals off from the outer tube.

The invention is not limited to the embodiment which has been shown by way of example, but can be modified within the scope of the attached patent claims.

What is claimed is:

1. A ventilation tube comprising: an outer tube with external treads proximate to an internal end for anchoring into a bone of the ear; and an inner tube releasable with the outer tube and having a through-channel for air communication between the cavity of the middle ear and the outside air, wherein the inner tube includes a flange at one end that prevents an opposite end of the inner tube from inadvertently being pushed too far into the middle ear yet past the internal end of the outer tube.

2. Device according to claim 1, wherein the inner tube is a polymer material selected from polyurethane or polyfluroethylene.

3. Device according to claim 1, wherein a front portion of the outer tube is provided with an external thread and an unthreaded end portion that provides a hollow extension from the external threads.

4. Device according to claim 3, wherein, the end portion of the front portion is surface-coated with a material which prevents tissue from growing over it.

5. Device according to claim 1, wherein a rear portion of the outer tube is of sufficient length that after anchoring the outer tube in the bone tissue, it extends from the bone/skin interface, through the skin, and out to the open air.

6. Device according to claim 1, wherein the inner tube has a length that extends the length of the outer tube.

7. Device according to claim 3, wherein an end of the outer tube opposite the untreaded end portion is capable of receiving various inserts selected from the group consisting of filters, membranes, capillaries, air pump and plug.

8. Device according to claim 3, wherein the inner tube is capable of receiving inserts selected from the group consisting of filters, membranes, capillaries, air pump, and plug.

9. Device according to claim 3, wherein the unthreaded end portion has a rounded shape and a gentle transition to the inner bore to prevent the inner tube from being scraped against the edge of the opening and causing a risk of detached tissue material remaining in the middle ear when the inner tube is removed.

10. Device according to claim 4, wherein the end portion is surface-coated with a polymeric material.

* * * * *